US008401826B2

(12) United States Patent
Cheng et al.

(10) Patent No.: US 8,401,826 B2
(45) Date of Patent: Mar. 19, 2013

(54) SYSTEM AND METHOD FOR REPRESENTATION, MODELING AND APPLICATION OF THREE-DIMENSIONAL DIGITAL PONTICS

(75) Inventors: Jihua Cheng, San Jose, CA (US); Vadim Matov, San Jose, CA (US); Eric Kuo, Foster City, CA (US); Woncheol Choi, San Jose, CA (US)

(73) Assignee: Align Technology, Inc., San Jose, CA (US)

( * ) Notice: Subject to any disclaimer, the term of this patent is extended or adjusted under 35 U.S.C. 154(b) by 1298 days.

(21) Appl. No.: 11/615,499

(22) Filed: Dec. 22, 2006

(65) Prior Publication Data

US 2008/0154419 A1  Jun. 26, 2008

(51) Int. Cl.
*G06F 17/50* (2006.01)
*G06F 7/48* (2006.01)
*A61C 11/00* (2006.01)
*A61C 5/00* (2006.01)
*G06F 19/00* (2011.01)
*G06T 15/00* (2011.01)
*G06T 17/00* (2006.01)

(52) U.S. Cl. ............ 703/1; 703/7; 433/213; 433/215; 700/98; 345/419; 345/420

(58) Field of Classification Search .............. 703/1, 7; 433/3, 6, 24, 201.1, 202.1, 215
See application file for complete search history.

(56) References Cited

U.S. PATENT DOCUMENTS

| | | | | | |
|---|---|---|---|---|---|
| 3,661,198 | A | * | 5/1972 | Evenson | 164/246 |
| 5,027,281 | A | * | 6/1991 | Rekow et al. | 700/182 |
| 5,273,429 | A | * | 12/1993 | Rekow et al. | 433/215 |
| 5,431,562 | A | * | 7/1995 | Andreiko et al. | 433/24 |
| 5,975,893 | A | * | 11/1999 | Chishti et al. | 433/6 |

(Continued)

OTHER PUBLICATIONS

International Preliminary Report on Patentablility from the International Bureau of WIPO dated Jun. 24, 2009 for relating International Application No. PCT/US2007/088441.

*Primary Examiner* — Omar Fernandez Rivas
*Assistant Examiner* — Akash Saxena
(74) *Attorney, Agent, or Firm* — Klein, O'Neill & Singh, LLP

(57) ABSTRACT

Modeling pontics at successive treatment stages includes: (1) calculating space measurements between first and second teeth by getting first and second tooth transformations at a treatment stage i; (2) applying the first and second tooth transformations to get positions of the first and second teeth at the stage i; (3) calculating a direction vector of the space measurements at the stage i; (4) calculating a reference plane using the direction vector as a normal; (5) determining whether the space is available for a pontic by measuring the distance from the closest point on each of the first and second teeth to the reference plane; (6) generating an original pontic geometry for a first treatment stage; and (7) generating pontic geometries at each successive stage by calculating deformation parameters based on the original pontic geometry and size characteristics of the space and of the first and second teeth at each stage.

25 Claims, 15 Drawing Sheets

U.S. PATENT DOCUMENTS

| | | |
|---|---|---|
| 6,049,743 A | 4/2000 | Baba |
| 7,155,373 B2 * | 12/2006 | Jordan et al. ............. 433/24 |
| 7,373,286 B2 * | 5/2008 | Nikolskiy et al. .......... 703/7 |
| 2002/0025503 A1 * | 2/2002 | Chapoulaud et al. ....... 433/24 |
| 2002/0055800 A1 * | 5/2002 | Nikolskiy et al. .......... 700/98 |
| 2002/0081546 A1 * | 6/2002 | Tricca et al. ............... 433/6 |
| 2006/0105294 A1 * | 5/2006 | Burger et al. ............. 433/167 |
| 2006/0188848 A1 * | 8/2006 | Tricca et al. ............. 433/24 |
| 2006/0194163 A1 * | 8/2006 | Tricca et al. ............. 433/24 |
| 2008/0138767 A1 * | 6/2008 | Kuo et al. ................. 433/215 |
| 2009/0111071 A1 * | 4/2009 | Yau et al. ................. 433/173 |

* cited by examiner

SYSTEM AND METHOD FOR REPRESENTATION, MODELING AND APPLICATION OF THREE-DIMENSIONAL DIGITAL PONTICS

TECHNICAL FIELD

The present invention relates, generally, to orthodontic treatment, and in particular to a system and method for representation, modeling and/or application of three-dimensional digital pontic of a tooth to facilitate orthodontic treatment.

BACKGROUND OF THE INVENTION

In the field of orthodontic treatment, it is sometimes necessary to extract one or more teeth prior to tooth repositioning. In some treatment cases, patients have previously had one or more teeth removed, also leaving a void or space between teeth. Also it is possible, in some cases, for an abnormal space to exist between two neighboring teeth due to irregular growth of one or more teeth. To fill the void when a tooth aligner is utilized, an artificial tooth or other structural component is used which is commonly referred to as a dental pontic. The ability to utilize such pontics during orthodontic treatment is desirable in these orthodontic applications, with such pontic cases comprising approximately 10% of all treated orthodontic cases.

In the case of polymeric shell aligners, the dental pontics used are different from the traditional physical dental pontic, which is an actual physical pontic positioned on the patient arch. In contrast, dental pontics are herein utilized to control the forming of pontics in polymeric shell aligners. For example, the design and fabrication of dental pontics is disclosed in U.S. Pat. No. 6,790,035, entitled "Method and Kits for Forming Pontics in Polymeric Shell Aligners" and assigned to Align Technology, Inc. For example, in such applications, a polymeric shell dental appliance that is removably placeable over a patient's dentition. The clinician manually determines the location in the appliance where the tooth is missing, as well as visually determining the size, position and shape characteristics of the space between teeth, e.g., the height, width, depth, contour, surface and like characteristics. After the space (or spaces) is identified, one pontic (or more pontics) is formed by filling the space within a trough of the appliance with a material, such as curable silicone compositions, to resemble a tooth.

As one would appreciate, the width and shape of the space between teeth gradually decreases or increases during various stages of treatment, thus requiring a process of manually determining the space or gap characteristics, such as size, shape and position, to provide an updated pontic geometry. Such manual determination is labor and time intensive and is subject to difficulties in making changes to pontic parameters when reviewing pontic geometries. In addition, the explicit and practicable methods utilized to construct the parametric pontic, in terms of representation and modeling, are very critical for forming polymeric shell aligners.

SUMMARY OF THE INVENTION

In accordance with various aspects of the present invention, systems and methods for representation, modeling and/or application of three-dimensional digital pontics to facilitate orthodontic treatment are provided. Such systems and methods for representation, modeling and application of three-dimensional digital pontic of a tooth can automatically facilitate a three-dimensional changeable and stage-dependent pontic geometry that provides various advantages over conventional manual methods for providing pontics.

In accordance with an exemplary embodiment, a system and method for representation, modeling and/or application of three-dimensional digital pontics automatically generates digital tooth models, and then using such digital tooth models automatically generates pontic models as deemed appropriate or desirable by the system. Upon generating such pontic models, a physical model, such as a stereolithography (SLA) model, can be provided so that polymeric shell aligners can be formed with pontics for various stages of treatment.

In accordance with an exemplary embodiment, a method for generation of pontic models and/or geometries automatically determines whether locations for pontics are advisable or desirable, i.e., whether a practitioner would find pontic use to be preferable or otherwise desirable during treatment of a patient. Once a location for a pontic is automatically determined, an original pontic geometry is automatically generated. Thereafter, stage dependent pontic geometries are automatically generated and positioned appropriately during the various stages of treatment as long as such pontics are desired.

BRIEF DESCRIPTION OF THE DRAWINGS

The exemplary embodiments of the present invention will be described in connection with the appended drawing figures in which like numerals denote like elements, and wherein.

DETAILED DESCRIPTION

The present invention may be described herein in terms of various components and processing steps. It should be appreciated that such components and steps may be realized by any number of hardware and software components configured to perform the specified functions. For example, the present invention may employ various electronic control devices, visual display devices, input terminals and the like, which may carry out a variety of functions under the control of one or more control systems, microprocessors or other control devices. In addition, the present invention may be practiced in any number of orthodontic contexts and the exemplary embodiments relating to a system and method for representation, modeling and/or application of three-dimensional pontic geometry to facilitate orthodontic treatment as described herein are merely a few of the exemplary applications for the invention. For example, the principles, features and methods discussed may be applied to any orthodontic treatment application.

In accordance with various aspects of the present invention, systems and methods for representation, modeling and/or application of three-dimensional digital pontic of a tooth to facilitate orthodontic treatment are provided. Such systems and methods for representation, modeling and application of pontic geometry of the tooth can automatically facilitate a changeable and stage-dependent pontic geometry that provides various advantages over conventional methods for providing pontics.

Figure 1A:
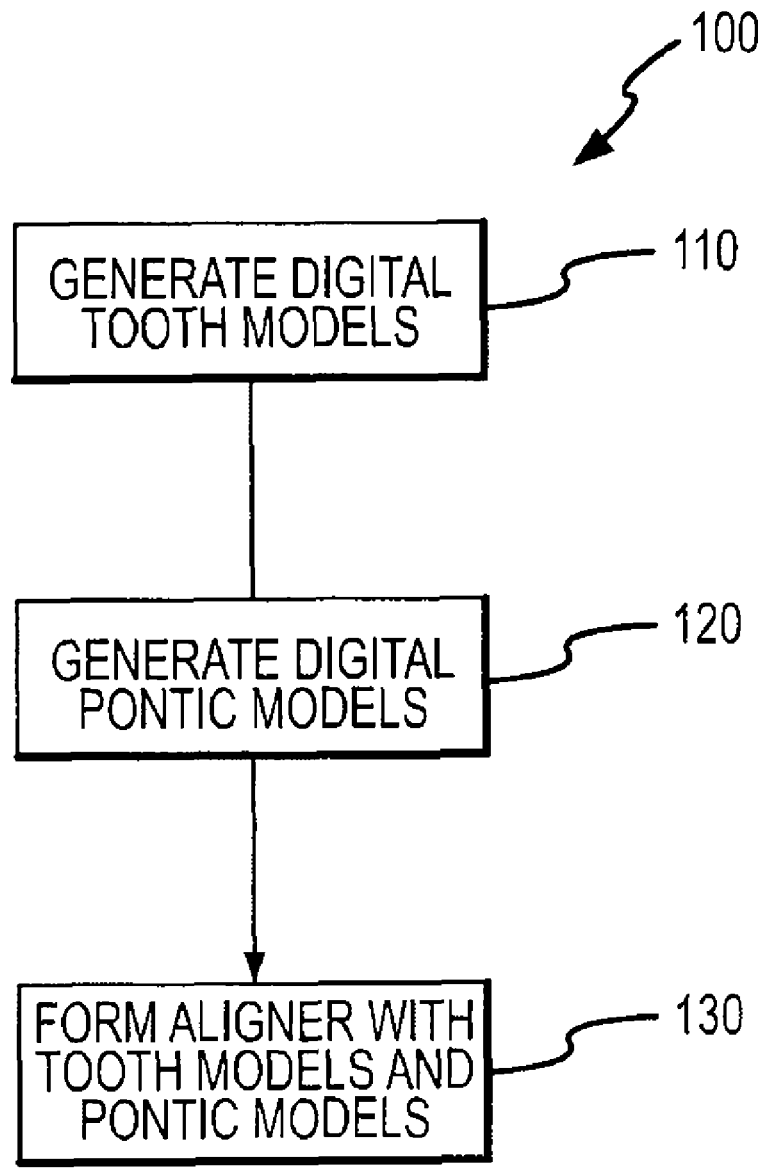
FIGS. 1A and 1B illustrate flow diagrams of exemplary methods for representation, modeling and/or application of pontic in accordance with exemplary embodiments of the present invention.

In accordance with an exemplary embodiment, with reference to FIG. 1A, a method 100 for representation, modeling and/or application of pontic automatically generates digital patient tooth models (110), and then using such digital tooth models automatically generates digital pontic models within such digital tooth models (120). Upon generating such pontic models, polymeric shell aligners can be formed with pontic models and patient tooth models for various stages of treatment (130).

Method (100) and/or the processes within can be suitably provided from one or more systems configured for providing the disclosed functions. As will be discussed later, such systems can comprise various control system configurations comprising one or more microprocessors, memory systems and/or input/output devices for processing and/or modeling data and information, and can comprise one or more software algorithms configured for modeling of pontic geometry and/or performing other functions set forth herein.

Figure 1B:
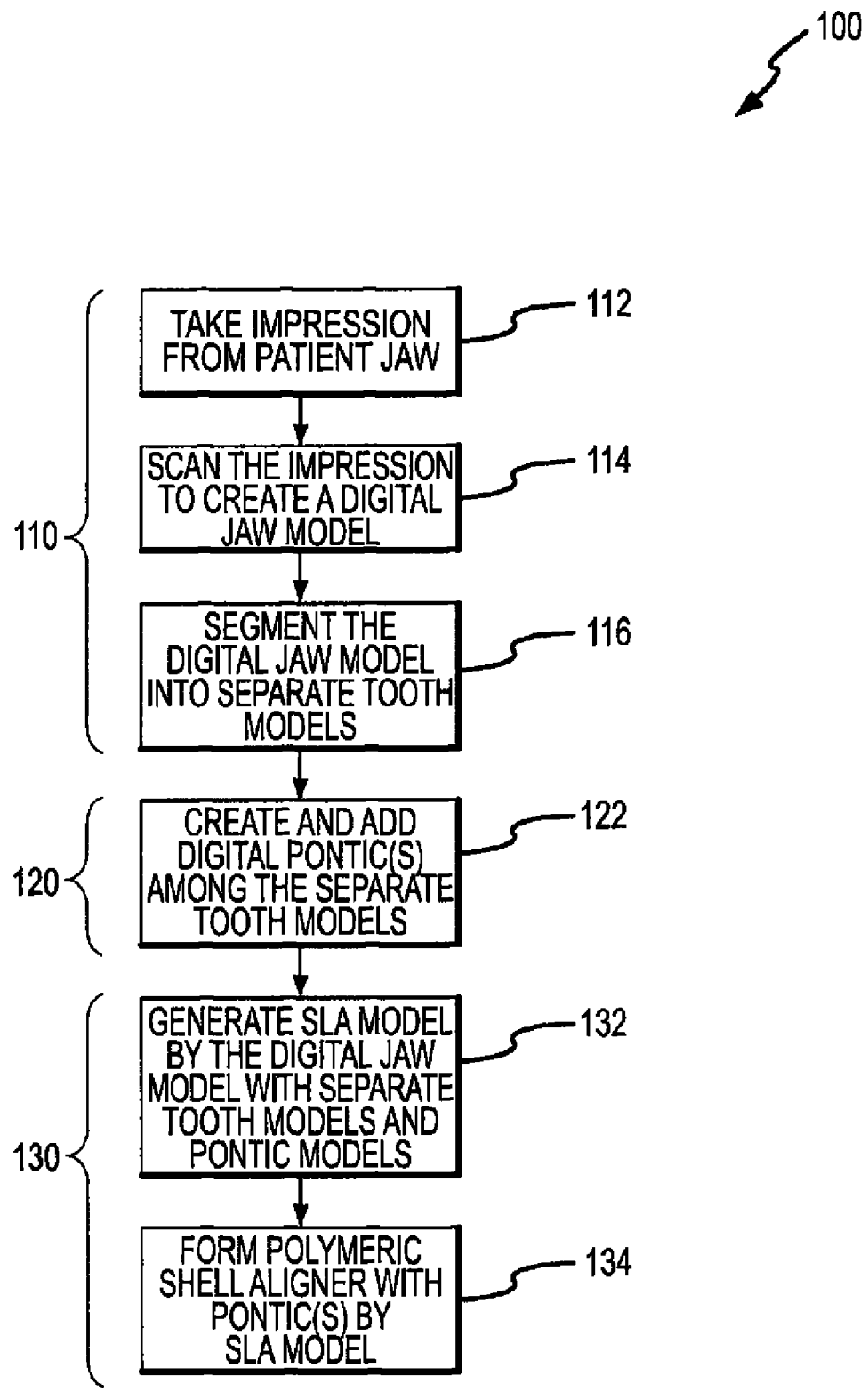

With reference to FIG. 1B, in accordance with an exemplary embodiment, the generation of digital patient tooth models (110) comprises the taking of impression of the patient jaw (112), the scanning of the impression to create digital jaw model (114) and the segmenting of the digital jaw model into separate tooth models (116). However, the generation of digital tooth models (110) can comprise any other methods for generation of such models.

For example, a digital data set representing a tooth arrangement can be obtained, often referred to as the initial digital data set (IDDS) for the teeth. Such an IDDS may be obtained in a variety of ways. For example, the patient's teeth may be scanned or imaged using well known technology, such as X-rays, three-dimensional x-rays, computer-aided tomographic images or data sets, magnetic resonance images, intra-oral scans, etc. Methods for digitizing such conventional images to produce data sets are well known and described in the patent and medical literature. By way of example, one approach is to first obtain a plaster cast of the patient's teeth by well known techniques, such as those described in Graber, Orthodontics: Principle and Practice, Second Edition, Saunders, Philadelphia, 1969, pp. 401-415. After the tooth casting is obtained, it can be digitally scanned using a conventional laser scanner or other range acquisition system to produce the IDDS. The data set produced by the range acquisition system may, of course, be converted to other formats to be compatible with the software that is used for manipulating images within the data set. General techniques for producing plaster casts of teeth and generating digital models using laser scanning techniques are also described, for example, in U.S. Pat. No. 5,605,459.

In accordance with an exemplary embodiment, with continued reference to FIG. 1B, the generation of pontic models (120) can comprise the automatic creation and addition of digital pontic(s) among the separate tooth models (122), e.g., among the separate tooth models generated in (116), while the forming of an aligner with tooth and pontic models (130) can comprise the generation of a physical jaw model, e.g., a stereolithography (SLA) model, by the digital jaw model with separate tooth models and pontic models (132) to facilitate formation of the polymeric shell aligners (134).

Figure 1C:
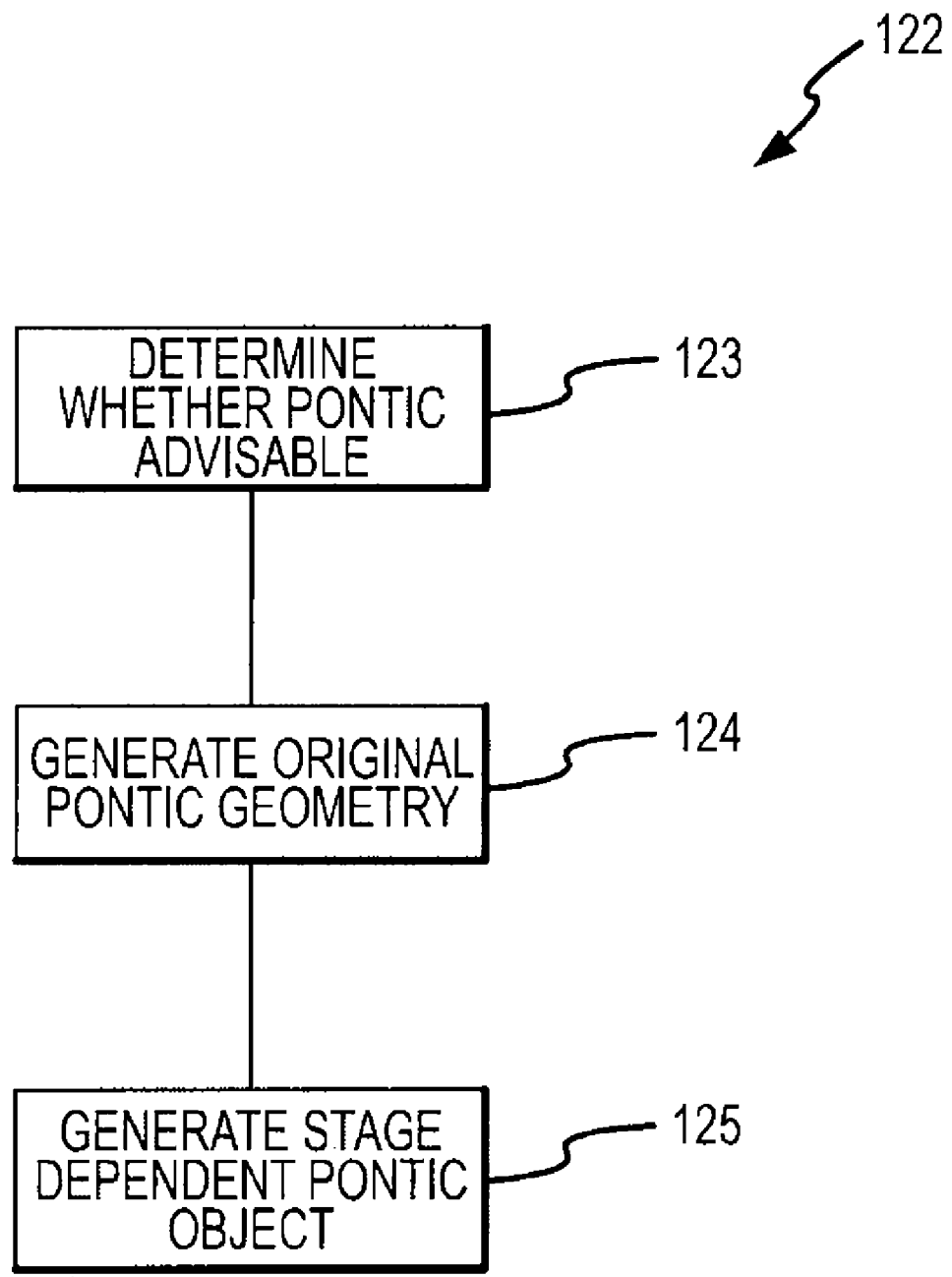
FIGS. 1C and 1D illustrate flow diagrams of exemplary methods for automatic generation of pontic geometry in accordance with exemplary embodiments of the present invention.

The automatic creation and addition of digital pontics among the separate tooth models (122) can be provided in various manners. In accordance with an exemplary embodiment, with reference to FIG. 1C, a method (122) for automatic creation and addition of digital pontics automatically determines whether one or more pontics are advisable, i.e., whether a practitioner would find pontic use to be preferable or otherwise desirable in the treatment of the patient or otherwise specifies or detects a desired location for a pontic (123). In other words, method (122) automatically detects for any spaces between the teeth of a patient to determine whether a pontic object would be useful or desirable within that space during the patient treatment process. Once a location for a pontic is automatically determined or specified, an original pontic geometry is automatically generated (124). Next, stage dependent pontic geometries can be automatically generated (125) during any pontic-advisable stages of treatment. Such a method (122) can be suitably conducted for more than one location/pontic, i.e., method (122) can be conducted for a single pontic location through completion of all stages, or can be conducted for multiple pontic locations at the same time for each stage before proceeding to a subsequent stage. However, for simplicity reasons, the various exemplary embodiments will be illustrated using a single pontic application and the calculation for pontics from an original stage through completion to a final stage.

Figure 2A:
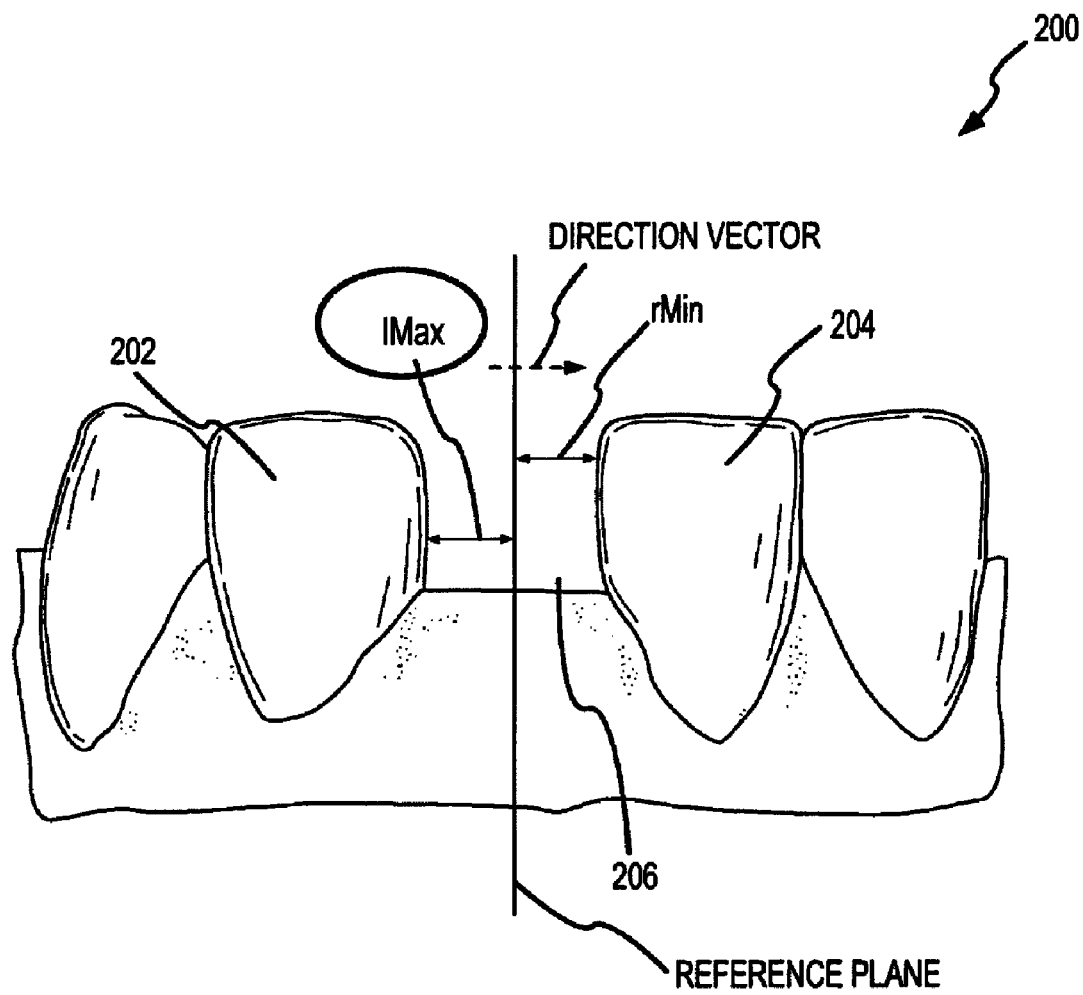
FIG. 2A illustrates a graphical representation of an exemplary tooth models with pontic space and the calculation of space in accordance with an exemplary embodiment of the present invention.
Figure 2B:
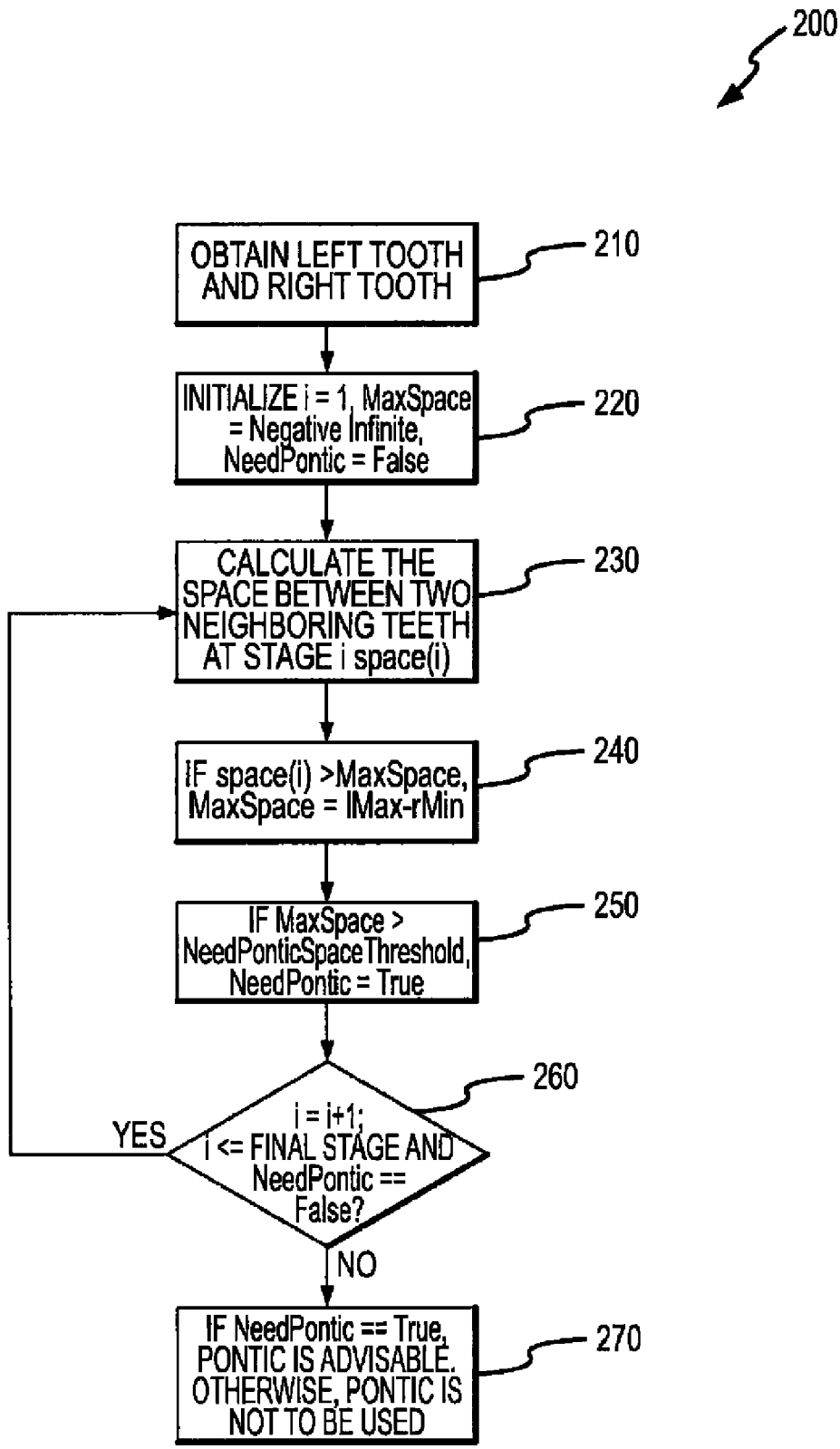
FIG. 2B illustrates a flow diagram of an exemplary method for automatically determining whether a pontic is advisable in accordance with an exemplary embodiment of the present invention.

With reference FIG. 2A of an illustration of digital tooth models 200, a space 206 can be automatically identified between two neighboring teeth, e.g., a left or first tooth 202 and a right or second tooth 204. Space 206 is then utilized to automatically detect whether a pontic is advisable or otherwise desirable between the two neighboring teeth. Such automatic detection can be conducted in various manners. For example, with reference to FIG. 2B, a method 200 for automatically determining whether one or more pontics are advisable or desirable comprises obtaining the two segmented digital neighboring teeth (210), e.g., the digital data for left tooth 202 and right tooth 204 obtained in (110) of FIGS. 1A and 1B, and the initializing of the detection process (220), e.g., the initializing the stage i=1, and two variables MaxSpace=Negative Infinite and NeedPontic=False. Next, the calculation of the space between the two neighboring teeth (230) is conducted, e.g., calculation of space(i) at stage i, followed by comparison to a pre-defined threshold for defining if a pontic is advisable or desirable within the space (240-260). For example, if the space at any stage, e.g., the value of MaxSpace, of the treatment is greater than a pre-defined threshold, e.g., the value of NeedPonticSpaceThreshold, such as can be determined in (250), one pontic or more pontics are advisable, desirable or can otherwise be utilized between the two neighboring teeth, e.g., the variable NeedPontic is true. On the other hand, if the space at any stage, e.g., the value of MaxSpace, of the treatment is less than the pre-defined threshold, e.g., the value of NeedPonticSpaceThreshold, no pontic is advisable, desirable, or otherwise will be utilized. The threshold value for the pontic use determination, NeedPonticSpaceThreshold, can be specified by user at any suitably value or selected by default. Method (200) can also be configured to confirm whether the pontic use determination has been conducted all the way through to the final stage or whether the calculation process should continue for interim stages (260). Accordingly, method (200) can determine whether a pontic is advisable, desirable, or otherwise will be utilized (270).

The calculation of two neighboring teeth (230) can be conducted in various manners. In accordance with another exemplary aspect of the embodiment, with reference to FIG. 2C, the calculation of space between two neighboring teeth (230) can be conducted by 1) obtaining digital models of two neighboring teeth (231), e.g., a left tooth 202 and a right tooth 204; 2) getting a left tooth transformation lTRW on the left tooth geometry at a given stage i and the right tooth transformation rTR(i) at stage I(232); 3) applying lTR(i) on the left tooth geometry and rTR(i) on the right tooth geometry (233) to get the two neighboring tooth positions at stage i; 4) calculating the direction vector of space measurement at stage i (234); 5) calculating the reference plane of the space measurement (235) by using the direction vector as a normal; 6) iterating each vertex on the right tooth to find the minimum signed distance (rMin) from the vertex to the reference plane (236); 7) iterating each vertex on the left tooth to find the maximum signed distance (lMax) from the vertex to the reference plane (237); and 8) calculating the space at stage i, (space (i), as rMin−lMax.

Figure 4A:
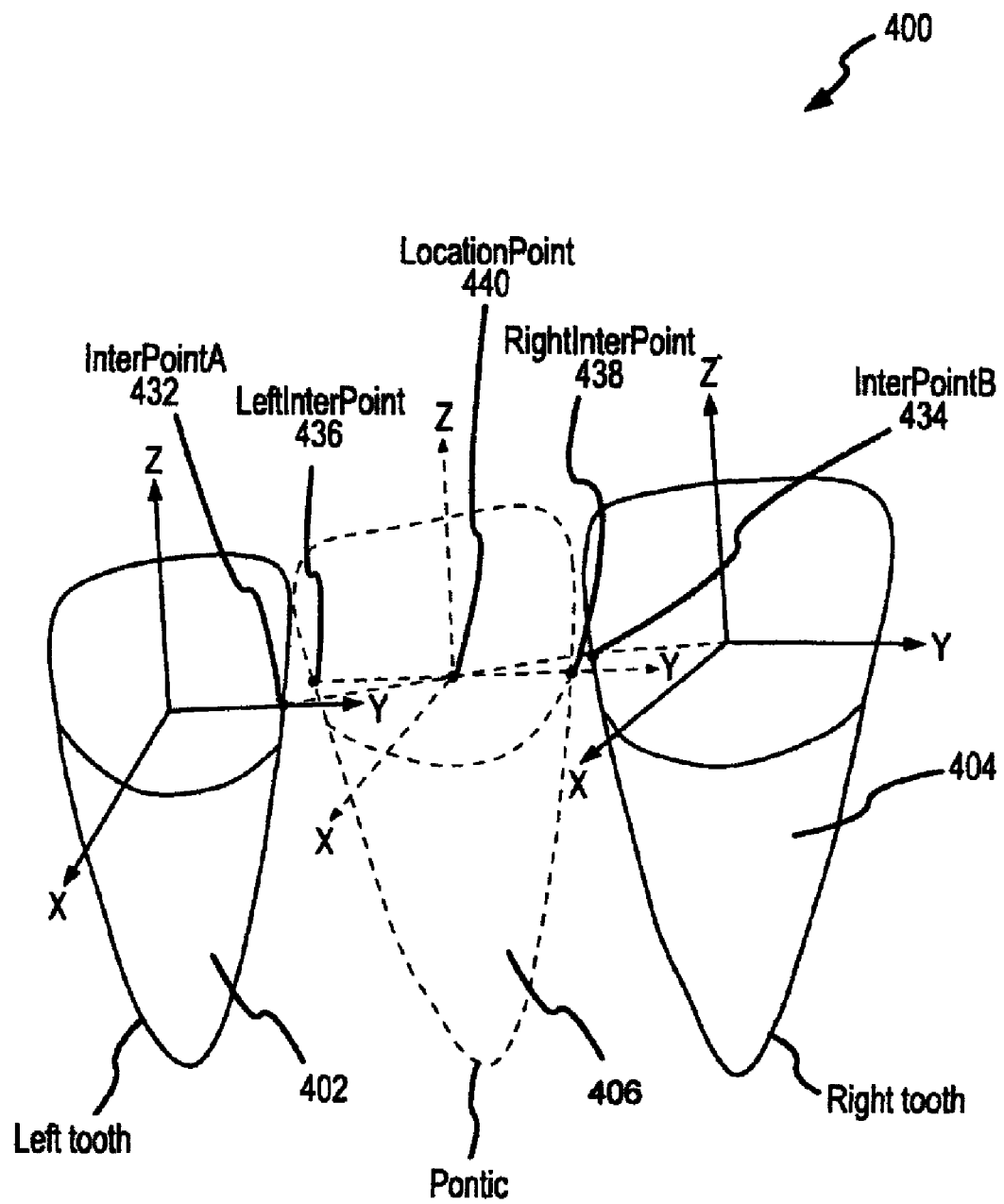
FIG. 4A illustrates a graphical representation of an exemplary positioning of pontic object in accordance with an exemplary embodiment of the present invention.

The calculation of direction vector of space measurement (234) can be conducted in various manners. For example, it can be the linear interpolation of the Y axis vector (LeftYAxisVector) of the left tooth's local coordinate system and the Y axis vector (RightYAxisVector) of the right tooth's local coordinate system. Examples of the left and right tooth local coordinate systems are illustrated in FIG. 4A. Accordingly, the space calculation can then be provided to further facilitate the determination of whether a pontic is advisable or otherwise desirable, such as through operation of steps (240-270 of FIG. 2B).

Figure 3:
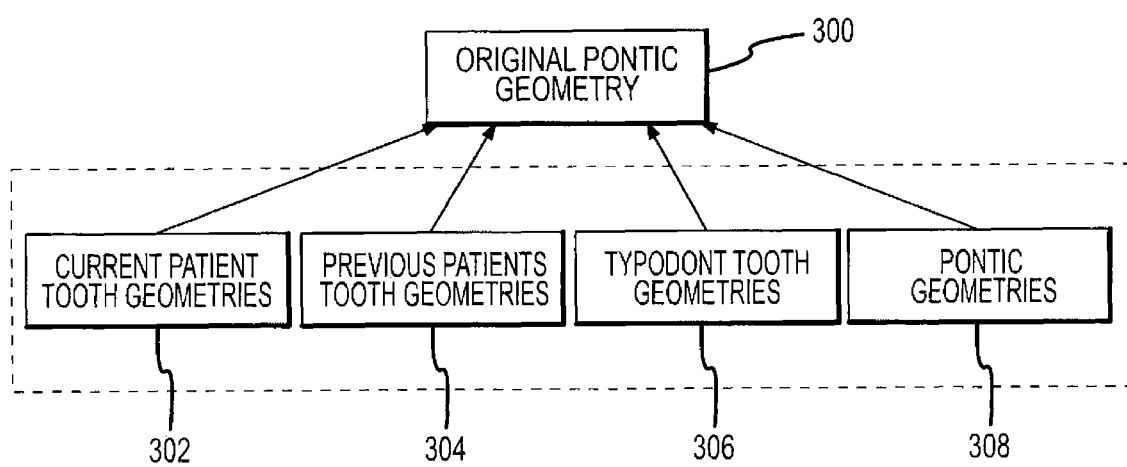
FIG. 3 illustrates a block diagram of resources for generating an original pontic geometry in accordance with exemplary embodiments of the present invention.

Referring again to FIG. 1C, once method (122) determines whether a pontic is desirable (123), i.e., detects or specifies a location for a pontic, the automatic generating of an original pontic geometry (124) is conducted. The original pontic geometry comprises the initial geometry prior to any deformation of the pontic geometry. In accordance with an exemplary embodiment, the original pontic geometry can be automatically generated by specifying such a geometry from several sources or libraries. For example, the pontic models in the libraries can be created from many sources, such as typodont tooth, tooth model from current or previous patients, modeled pontic, and the like. The modeled tooth libraries can also be created by certain methods, such as scanning existing physical tooth model to generate a three-dimensional tooth geometry, utilizing computer aided design (CAD) software to model a three-dimensional tooth geometry, using certain algorithm to generate a three-dimensional tooth geometry, and the like. In other words, any one or more sources can be utilized to find a suitable configuration to automatically generate the original pontic geometry. For example, with reference to an exemplary embodiment illustrated in FIG. 3, an original pontic geometry 300 can be automatically selected from any tooth geometry from the current patient application 302, such as neighboring teeth, a symmetric tooth or any other tooth of the patient, or automatically selected from any tooth geometry of teeth from any previous patient application 304. In addition, the original pontic geometry can be automatically selected from a typodont tooth geometry library 306 and/or from a pontic library 308. Moreover, the automatic specifying and selection of such original pontic geometry within such sources 302, 304, 306 and/or 308, or any combination thereof, can be facilitated by using the measurements and other characteristics obtained through processes 122.

Figure 4B:
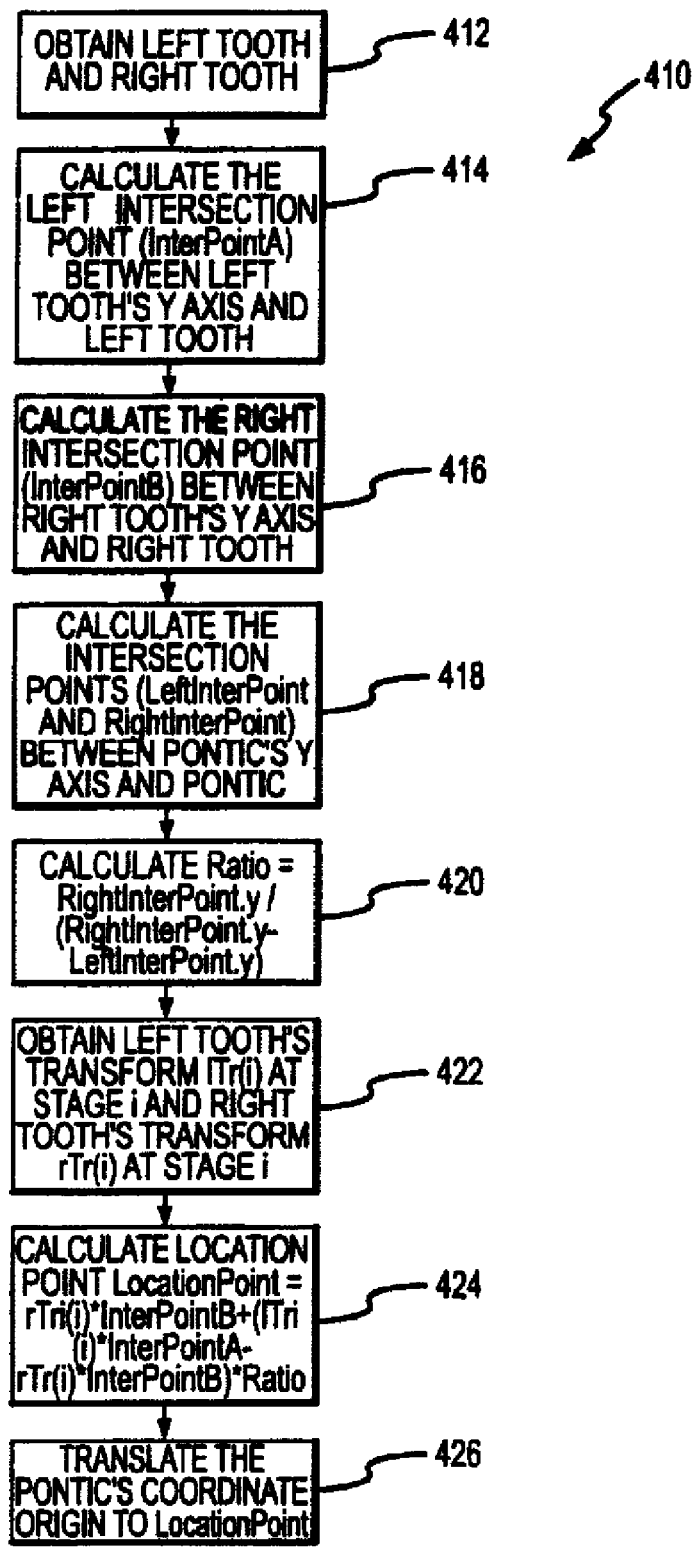
FIG. 4B illustrates a flow diagram of an exemplary method for automatically positioning a pontic between two teeth in accordance with an exemplary embodiment of the present invention.

Once a suitable pontic geometry is automatically selected, e.g., from within such sources 302, 304, 306 and/or 308, an original pontic geometry can be generated. For example, with reference to a digital representation of teeth illustrated in FIG. 4A, the original pontic geometry can be used to generate and position a pontic object 408 between left tooth 402 and right tooth 404. In accordance with an exemplary embodiment, with additional reference to FIGS. 4B and 4A, a method 410 for automatic positioning of a pontic at any pontic used stage (stage i) between two neighboring teeth can comprise the obtaining of the digital models for the left tooth 402 and the right tooth 404 in step (412), calculating a left intersection point 432 (InterpointA) and a right intersection point 434 (InterpointB) in steps (414) and (416), and calculating the intersection points 436 and 438 in step (418). Upon calculation of intersection points 436 (LeftInterPoint) and 438 (RightInterPoint), method 410 can calculate the pontic's origin (LocationPoint) of its local coordinate system by the linear interpolation of the InterpointA and InterpointB (420-424), and then translating the pontic's origin to the calculated LocationPoint (426). As a result of having provided the pontics coordinate origin, pontic 406 can be suitably positioned within the space between teeth 402 and 404.

It should be noted that while the process of generating the original pontic geometry may be conducted in many cases at the first stage of treatment, such conducting at the first stage is not required. Accordingly, the automatic generating and positioning of a pontic geometry (410) can be conducted or otherwise initiated during any stage of the treatment process. Pontic object 406 can be suitably assigned a tracking or other identification number, e.g. the tooth number corresponding to the removed tooth, for tracking of the pontic during deformation processes.

With reference again to FIG. 1C, having automatically generated the original pontic geometry (124), method (122) can then proceed to generate stage dependent pontic object (125) for the treatment stages determined by the clinician. For example, with reference again to FIG. 1D, in accordance with an exemplary embodiment, the automatic generation of stage dependent pontic object (125) for each stage of treatment can comprise the automated calculation of the space characteristics, e.g., the size, shape and width, between two neighboring teeth at each stage (131), the automated calculation of a pontic deformation scale (133) and the automated creation of the stage dependent pontic object (135) based on such space characteristics and deformation scale.

Figure 2C:
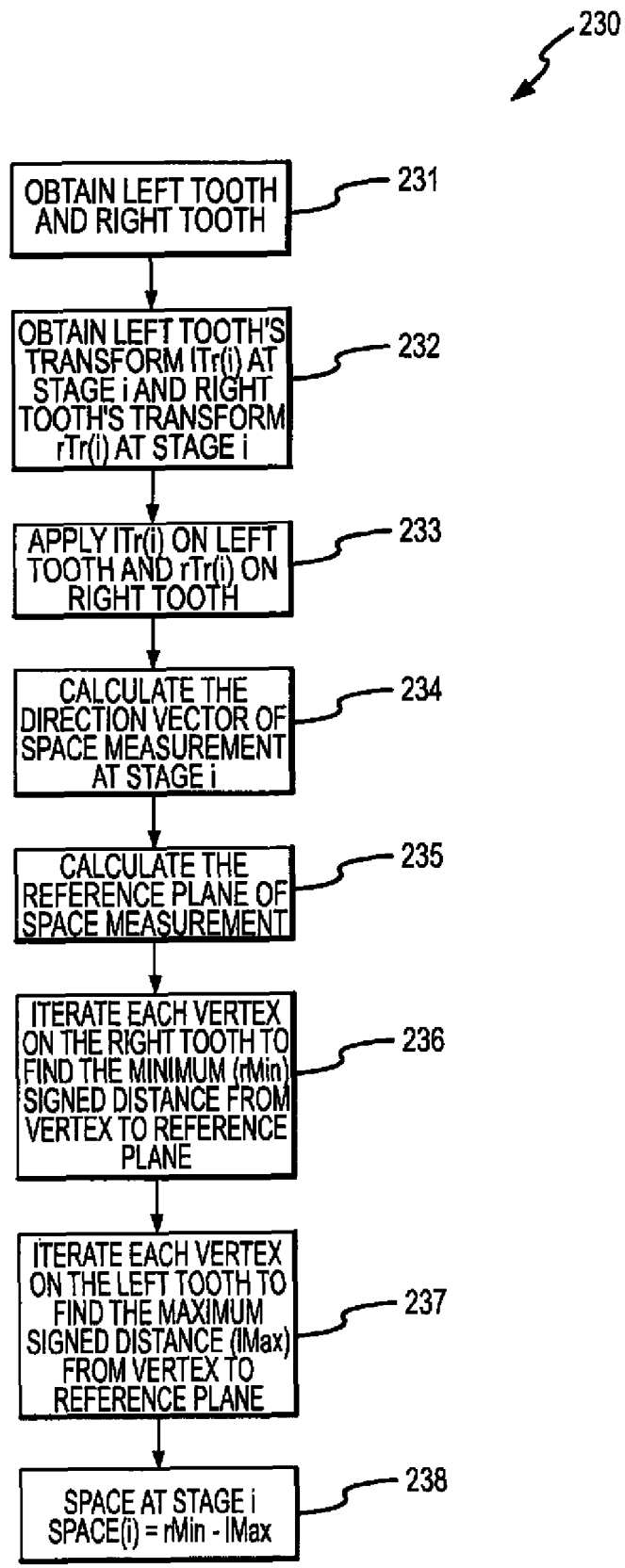
FIG. 2C illustrates a flow diagram of an exemplary method for automatically calculating the space between two teeth in accordance with an exemplary embodiment of the present invention.

The automated calculation of the space between two neighboring teeth at each stage can be suitably conducted using process (230) illustrated in FIG. 2C. Using the calculated space characteristics, the automated calculation of a pontic deformation scale (133) can be conducted. The pontic deformation scale will be utilized to construct the pontic geometry. In the exemplary embodiment, the deformation of the original pontic geometry can be realized by uniform scaling and non-uniform scaling. For uniform scaling, all the vertices of the pontic mesh are scaled with three parameters, namely X-scale, Y-scale and Z-scale. In uniform scaling, X-scale, Y-scale and Z-scale are constants. Non-uniform scaling uses four parameters, namely X-scale, Y-scale, Z-scale and Y-scale-range. However, for non-uniform scaling only the vertices of the pontic mesh beyond the Y-scale-range are scaled, and the vertices of the pontic mesh within the Y-scale-range are not scaled. For non-uniform scaling, the Y-scale amount of a pontic mesh vertex is not a constant. The Y-scale amount depends on the distance from the vertex to the X-Z plane. The further the distance from the vertex, the greater the Y-scale amount. The purpose of using Y-scale-range is to keep the pontic's appearance on its facial side.

Figure 5:
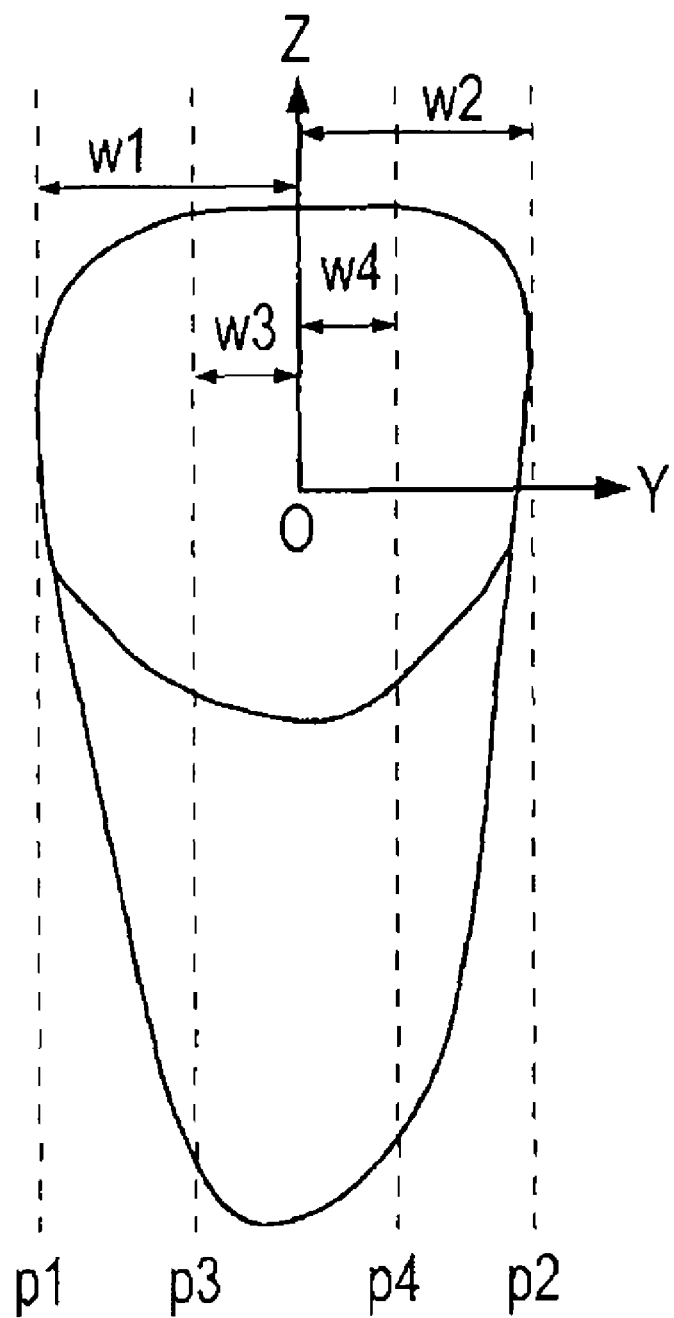
FIG. 5 illustrates a graphical representation of an exemplary pontic for demonstrating calculation of deformation scaling in accordance with an exemplary embodiment of the present invention.

For example, with reference to FIG. 5, an exemplary pontic can be viewed on a Y-Z plane. Assuming the Y-scale-range is r, where $1 \geq r \geq 0$, then $w3=w1*r$ and $w4=w2*r$. When non-uniform scaling is applied on the pontic, the vertices between plane p3 and plane p4 are not scaled, only the vertices between plane p1 and plane p3 and the vertices between plane p4 and plane p2 are scaled. In the example, the maximum Y-scale (Y-max-scale) is determined by the equation:

$$Y\text{-max-scale}=(\text{Space}-\text{SpaceTolerance})/\text{OriginalPonticWidth}$$

wherein the variable Space is the space between the two neighboring teeth, the variable SpaceTolerance is the amount for the tolerance of space or overlap, which may be 0, positive, or negative, and the variable OriginalPonticWidth is the width of the original pontic in Y axis direction. When the variable SpaceTolerance is a positive value, it means the space is allowed between the pontic and its neighboring tooth. When the variable SpaceTolerance is a negative value, it means overlap is allowed between pontic and its neighboring tooth.

Following the calculation of Y-max-scale, the Y-scale amount of a pontic mesh vertex can be determined by the equation:

$$Y\text{-scale}=\lambda*Y\text{-max-scale}$$

where $\lambda$ is a weight factor of distance, which can be determined by the equation:

$$\lambda=\text{dist}/\text{max-dist}$$

where dist is the distance from the vertex to plane p4 if the vertex is on the right side of plane p4 or the distance from the vertex to plane p3 if the vertex is on the left side of plane p3, and max-dist is the maximum distance w2 if the vertex is on the right side of plane p4 or the maximum distance w1 if the vertex is on the left side of plane p3. In particular, for uniform scaling, the $\lambda$ is a constant which is equal to 1.

In addition, X-scale can be calculated by the linear interpolation of the two neighboring tooth's depths in X axis direction. The equation X-scale can be determined by the equation:

$$X\text{-scale}=\lambda*\text{LeftToothDepth}+(1-\lambda)*\text{RightToothDepth}$$

wherein $1 \geq \lambda \geq 0$, the variable LeftToothDepth is the depth of left neighboring tooth in X axis direction, and the variable RightToothDepth is the depth of right neighboring tooth in X axis direction. Finally, z-scale can be calculated by the linear interpolation of the two crown heights of neighboring teeth in Z axis direction, such as by the equation:

$$Z\text{-scale}=\lambda*\text{LeftToothHeight}+(1-\lambda)*\text{RightToothHeight}$$

wherein $1 \geq \lambda \geq 0$, the variable LeftToothHeight is the crown height of left neighboring tooth in Z axis direction, and the variable RightToothHeight is the crown height of right neighboring tooth in Z axis direction.

Thus, using either uniform or non-uniform scaling, values for the parameters X-scale, Y-scale, Z-scale (and Y-scale-range is using non-uniform scaling) can be automatically determined and compared to previous XYZ-scale parameters, i.e., compared to those parameters for the original pontic geometry or any of the previous stage geometries, to assess the amount of deformation. Other geometric parameters besides XYZ-scale parameters can be suitably determined and automatically compared to generate a pontic deformation scale. Moreover, the relative weight or importance of any one or more parameters can be suitably scaled as desired by the clinician.

Figure 1D:
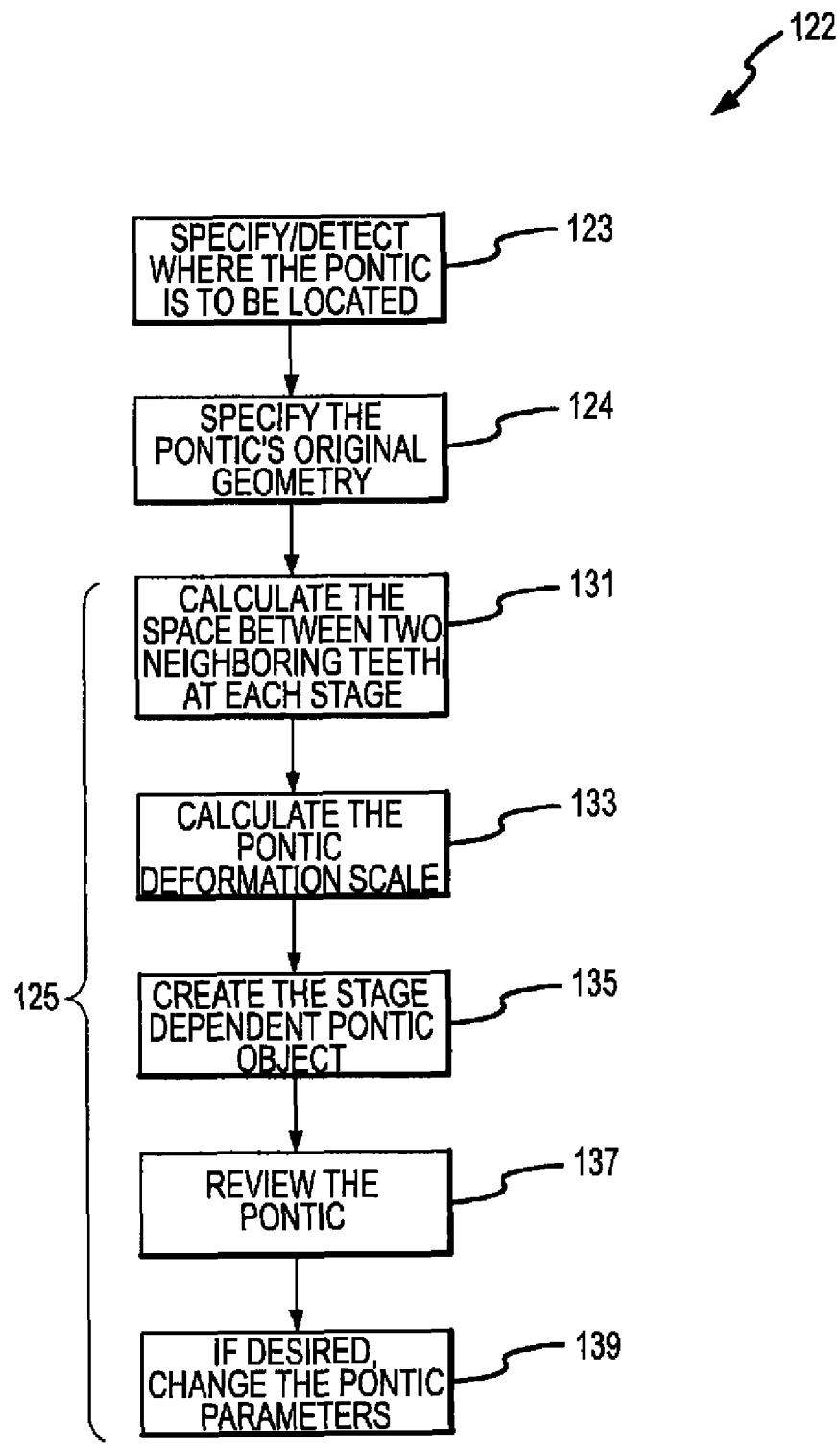
Figure 6A:
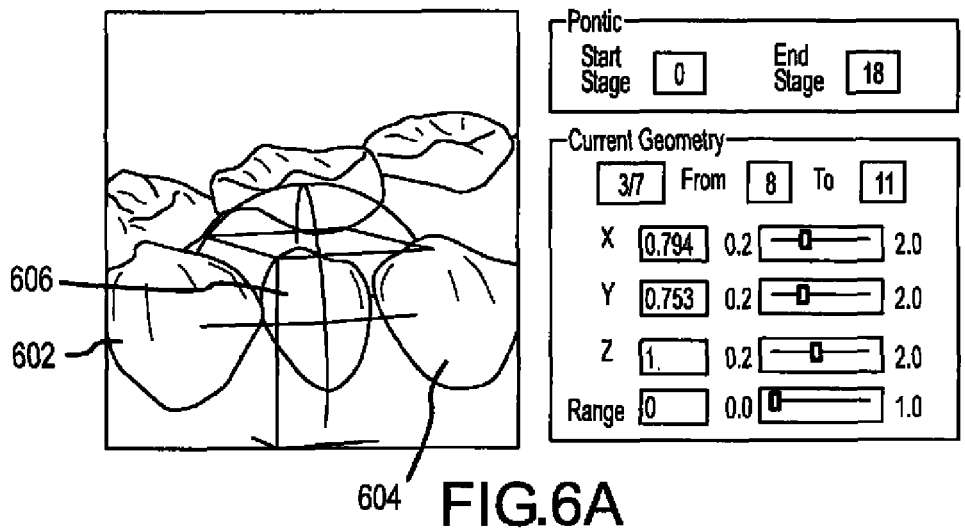
FIGS. 6A-6D illustrate graphical representations of stage dependent pontic geometry in accordance with an exemplary embodiment of the present invention.
Figure 6B:
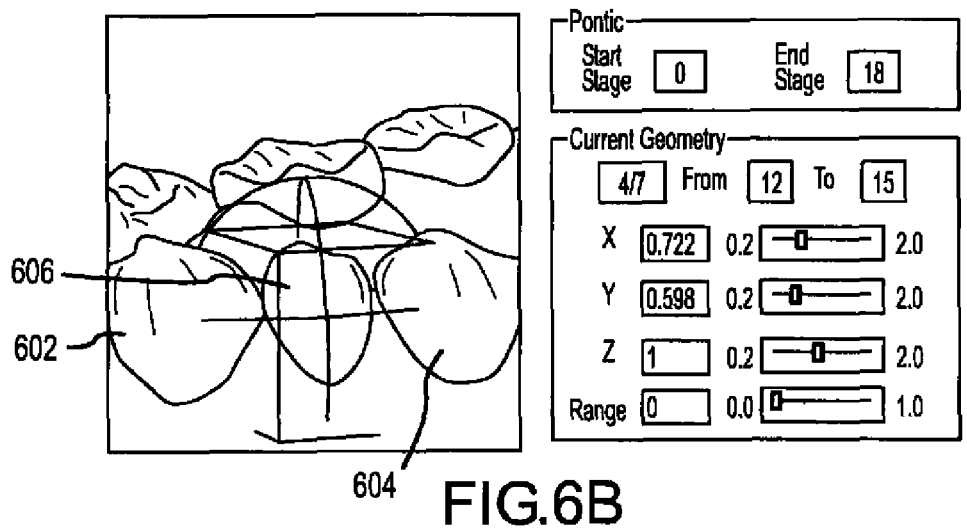
Figure 6C:
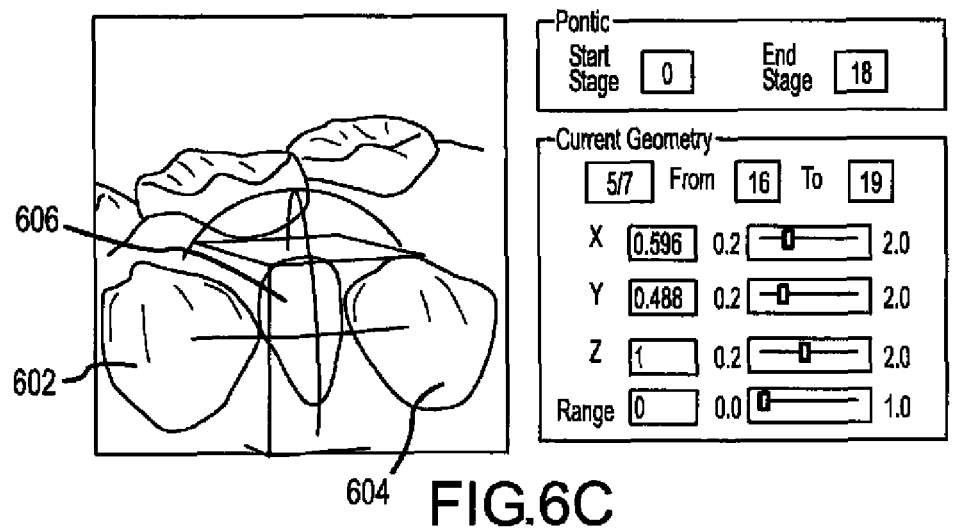
Figure 6D:
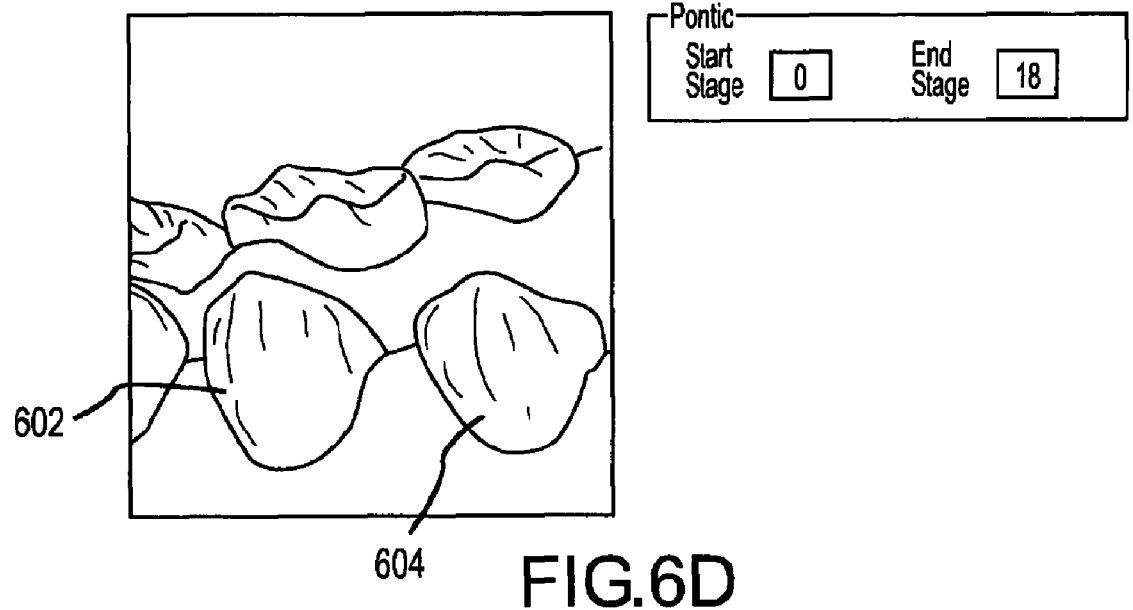

Having determined such a pontic deformation scale, with continued reference to FIG. 1D, automatic creation of the stage dependent pontic object (135) can be realized. Such a stage dependent pontic geometry can be realized by applying the pontic deformation scale to the corresponding original pontic geometry. For example, with reference to FIGS. 6A-6C, a graphical representation of stage dependent pontic geometries to generate pontic objects is illustrated, with FIG. 6A illustrating the deformed pontic geometry from stages 8 through 11 of an exemplary treatment process, FIG. 6B illustrating the deformed pontic geometry from stages 12 through 15 of the treatment process, and FIG. 6C illustrating the deformed pontic geometry from stages 16 through 18 of the treatment process. As illustrated in FIGS. 6A-6C, as the relative amount of spacing between teeth 602 and 604 decreases during treatment stages, the XYZ-scale parameters change to generate an updated (stage dependent) pontic deformation scale, with such scale then used to generate a deformed pontic geometry to provide a deformed pontic object 606 for a selected stage. Such a process can be continued for any remaining stages of treatment, for example, with continued reference to FIG. 1D, proceeding from creation of stage dependent pontic geometry (135) back to space calculation (131), until the spacing between teeth 602 and 604 no longer will utilize a pontic object, such as illustrated in FIG. 6D. Such a process to determine whether the spacing between teeth 602 and 604 can or should use a pontic object any longer can automatically and/or manually determined by comparison pre-selected parameter values, and which can occur at any stage(s) of treatment.

In accordance with an exemplary embodiment, with continued reference to FIG. 1D, the automatic generation of stage dependent pontic object (125) for each stage of treatment can further comprise a verification process. For example, with reference again to FIG. 1D, the automatic generation of stage dependent pontic object (125) for each stage of treatment can further comprise the reviewing of a pontic object (137) and if desired, change the pontic parameters (139) to generate a re-deformed stage dependent pontic geometry for providing a pontic object, such as a pontic 606 illustrated in FIG. 6B. Such a review of pontic object (137) can be conducted automatically, and/or allow for manual review, to confirm a pontic geometry has been appropriately generated. For example, assessments of the coordinate parameters XYZ can be made to compare to tolerances, e.g., space or overlap tolerances, or other criteria and determine whether a pontic geometry has been appropriately generated and positioned.

Figure 7:
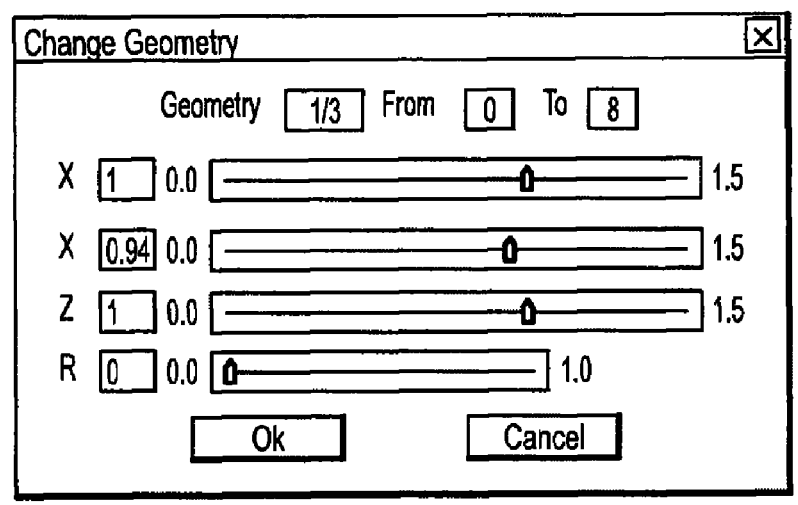
FIG. 7 illustrates an exemplary user interface page for controlling the scaling of deformation for pontic objects in accordance with an exemplary embodiment of the present invention.

With continued reference to FIG. 1D, in the event that the pontic geometry was not appropriately generated or otherwise not suitable for the treatment process, various changes to the pontic parameters (139) can be made to generate a re-deformed stage dependent pontic geometry. Such changes can include the suitable scaling of one or more parameters, e.g., the XYZ parameters and/or other pontic scaling parameters, as well as the scaling range, to generate the re-deformed stage dependent pontic geometry. For example, with reference to FIG. 7, a clinician can access the scaling parameters and ranges through a menu page to generate the re-deformed stage dependent pontic geometry.

Figure 8:
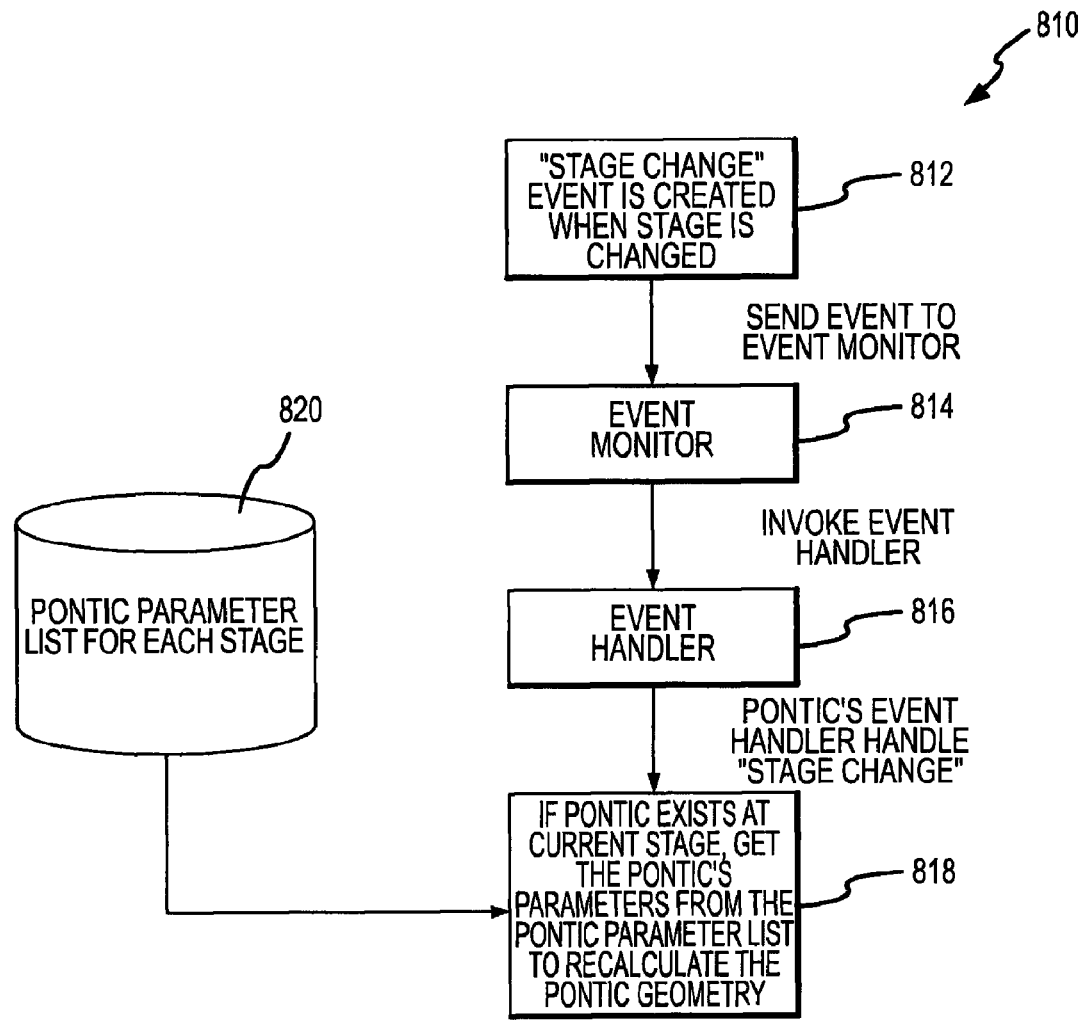
FIG. 8 illustrates a flow diagram of an exemplary method for a mechanism of stage dependent pontic modeling in accordance with an exemplary embodiment of the present invention.

With continued reference to FIG. 1D, the exemplary method for automatic generation of stage dependent pontic object (125) can also be conducted and/or implemented in various manners through a computer control system. For example, with reference to FIG. 8, an exemplary mechanism for stage dependent geometry (810) can comprise the creation of a "Stage Change" event when a stage is changed from one to another (812), with an "event" or other signal sent to an event monitor (814), with an event handler then being invoked (816). Next, an event handler associated with a pontic can determine whether a pontic exists at the current stage, and if so, then obtain the pontic parameters from a corresponding parameter list, e.g., from a list (820), to recalculate the pontic geometry (818). Various other mechanisms and processes can also be implemented within an exemplary control system.

With reference again to FIGS. 1A and 1B, having created pontics among the digital tooth models (120), a solid, physical jaw model, such as an SLA model can be generated (132). Such a physical tooth SLA model can be provided in various manners now known or hereinafter created, including that disclosed in U.S. Pat. No. 6,790,035, entitled "Method and Kits for Forming Pontics in Polymeric Shell Aligners" and assigned to Align Technology, Inc. Having generated the physical jaw model (132), method 100 can suitably form polymeric shell aligners (134), including the use of pontics as wanted or desired. Such forming of polymeric shell aligners using pontics can comprise various methods and processes for such pontic formations. For example, the design and fabrication of dental pontics can comprise one or more of the methods disclosed in U.S. Pat. No. 6,790,035, entitled "Method and Kits for Forming Pontics in Polymeric Shell Aligners" and assigned to Align Technology, Inc.

Figure 9:
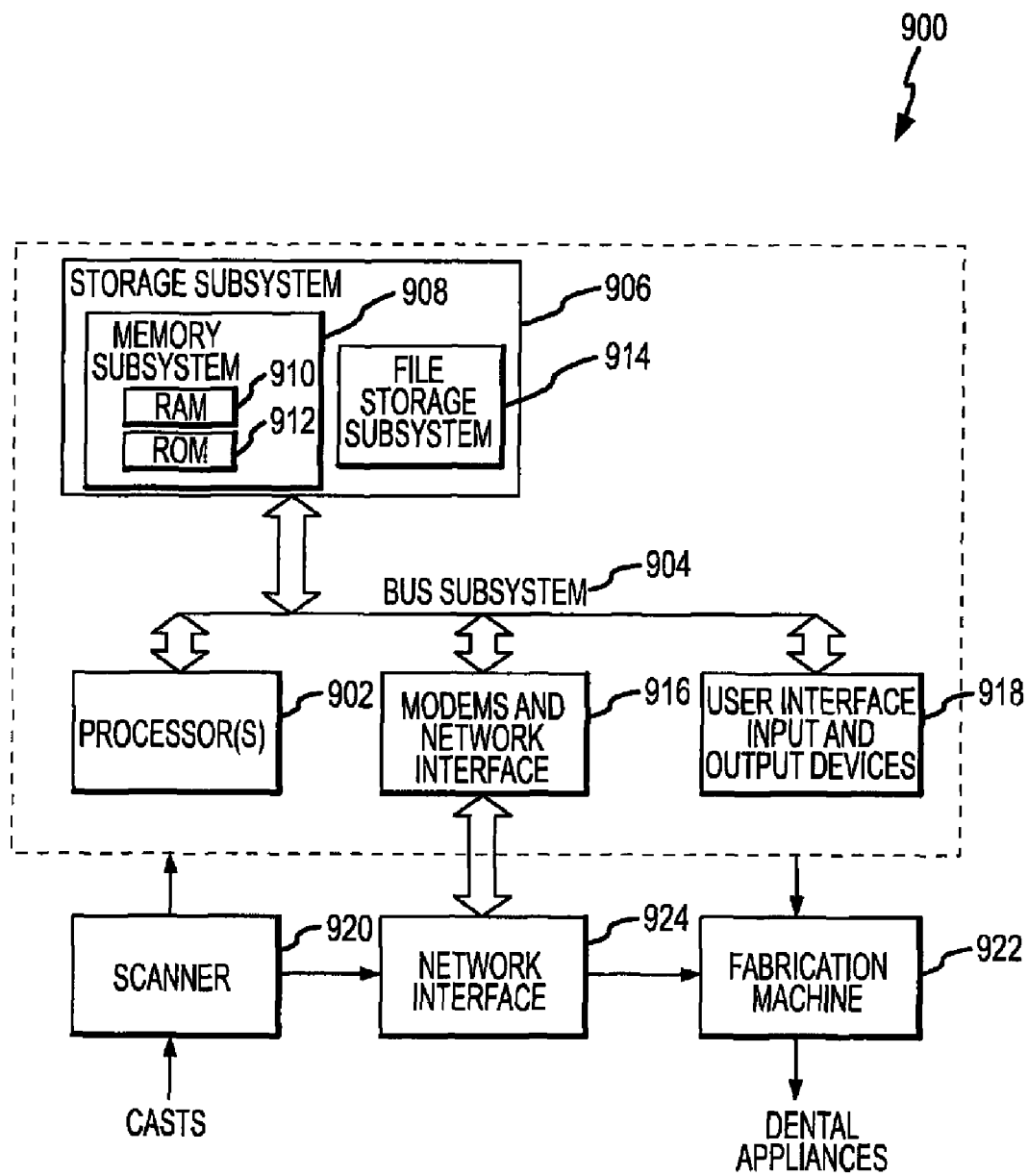
FIG. 9 illustrates an exemplary control system in accordance with an exemplary embodiment of the present invention.

Such exemplary methods for representation, modeling and/or application of pontic geometry to facilitate orthodontic treatment can be conducted with one or more computer-based systems through the use of one or more algorithms. For example, with reference to FIG. 9, an exemplary computerized system 900 for facilitating automated generation of the dynamic cutting curve and/or for dynamic adjustment of the cutting tool can comprise one or more computer-based systems or modules, microprocessors, memory systems and/or input/output devices for processing data and information, comprising one or more software algorithms configured for computing and/or performing other functions set forth herein. For example, exemplary computerized system 900 can comprise processor(s) 902, bus subsystems 904, memory or storage subsystems 906-914, network interfaces 916, input/output devices 918 and/or other components, and can be configured to communicate with other devices, such as scanner 920, network interface 924 and/or fabrication machine 922, as disclosed in U.S. Pat. No. 7,040,896, entitled "Systems and Methods for Removing Gingiva From Computer Tooth Models", and assigned to Align Technology, Inc., or any other computerized system components used for computational orthodontics.

The present invention has been described above with reference to various exemplary embodiments. However, those skilled in the art will recognize that changes and modifications may be made to the exemplary embodiments without departing from the scope of the present invention. For example, the various operational steps, as well as the components for carrying out the operational steps, may be implemented in alternate ways depending upon the particular application or in consideration of any number of cost functions associated with the operation of the system, e.g., various of the component and methodologies and/or steps may be deleted, modified, or combined with other components, methodologies and/or steps. For example, various of the methods, systems and devices, such as utilizing tooth local coordinate system, or tooth geometry libraries, can suitably utilize any other conventional techniques, or any later developed techniques. These and other changes or modifications are intended to be included within the scope of the present invention, as set forth in the following claims.

The invention claimed is:

1. A computerized system for modeling a pontic to facilitate orthodontic treatment of teeth of a patient through a sequence of treatment stages, the computerized system comprising a processor configured for:

calculating space measurements of a digital representation of a space located between a digital representation of a first tooth having a first geometry and a second tooth having a second geometry by getting a first tooth transformation of the first tooth at a given treatment stage i and a second tooth transformation of the second tooth at the treatment stage i, wherein the first tooth defines a first coordinate system having a first Y-axis and the second tooth defines a second coordinate system having a second Y-axis;

applying the first tooth transformation to the first geometry and applying the second tooth transformation to the second geometry to get first and second positions of the first and second teeth, respectively, at the stage i;

calculating a direction vector of the space measurements at the stage i, wherein the direction vector is derived from an interpolated Y-axis between the first Y-axis and the second Y-axis;

calculating a reference plane for the space measurements by using the direction vector as a normal;

determining whether the space is available for a pontic by measuring the distance from the closest point on each of the first and second teeth to the reference plane;

generating an original pontic geometry to provide a digital representation of an initial pontic object for use in a first stage of the sequence of treatment stages; and generating stage-dependent pontic geometries at each treatment stage during successive treatment stages of the sequence of treatment stages, by calculating deformation parameters based on the original pontic geometry, size characteristics of the space, and size characteristics of the first and second teeth at each of the treatment stages, to provide digital representations of stage-dependent pontic objects.

2. The computerized system of claim 1, wherein the processor is further configured for (a) measuring the distance from the closest point on each of the first and second teeth to the reference plane by iterating each vertex on the first tooth to find a maximum signed distance (lMax) from each vertex on the first tooth to the reference plane and by iterating each vertex on the second tooth to find a minimum signed distance (rMin) from each vertex on the second tooth to the reference plane, and (b) calculating the space measurements at the stage i as the difference between rMin and lMax.

3. The computerized system of claim 1, wherein the processor is further configured to select the original pontic geometry from a library of geometries.

4. The computerized system of claim 3, wherein the library of geometries comprises at least one of current patient tooth geometries, prior patient tooth geometries, typodont tooth geometries and pontic geometries.

5. The computerized system of claim 1, wherein the processor is further configured to calculate a size of the space in each treatment stage in the sequence of treatment stages.

6. The computerized system of claim 1, wherein the processor is further configured to position a digital representation of the initial pontic object within the space.

7. The computerized system of claim 1, wherein the processor is further configured to calculate the deformation parameters using uniform scaling.

8. The computerized system of claim 1, wherein the processor is further configured to calculate the deformation parameters using non-uniform scaling.

9. The computerized system of claim 1, wherein the processor is further configured to generate a deformed pontic geometry based on the deformation parameters.

10. The computerized system of claim 9, wherein the processor is further configured to re-scale the deformed pontic geometry.

11. The computerized system of claim 9, wherein the processor is further configured to scale the deformed pontic geometry based on scaling of at least one parameter comprising an X-scale parameter, a Y-scale parameter, and a Z-scale parameter, the at least one parameter being used with or without a Y-scale range parameter.

12. A computerized method for modeling a pontic to facilitate orthodontic treatment of teeth of a patient through a sequence of treatment stages, the method comprising:
calculating space measurements of a digital representation of a space located between a digital representation of a first tooth having a first geometry and a second tooth having a second geometry by getting a first tooth transformation of the first tooth at a given treatment stage i and a second tooth transformation of the second tooth at the treatment stage i, wherein the first tooth defines a first coordinate system having a first Y-axis and the second tooth defines a second coordinate system having a second Y-axis;
applying the first tooth transformation to the first geometry and applying the second tooth transformation to the second geometry to get first and second positions of the first and second teeth, respectively, at the stage i;
calculating a direction vector of the space measurements at the stage i, wherein the direction vector is derived from an interpolated Y-axis between the first Y-axis and the second Y-axis;
calculating a reference plane for the space measurements by using the direction vector as a normal;
determining whether the space is available for a pontic by measuring the distance from the closest point on each of the first and second teeth to the reference plane;
generating an original pontic geometry to provide a digital representation of an initial pontic object for use in a first stage of the sequence of treatment stages; and
generating stage-dependent pontic geometries at each treatment stage during successive treatment stages of the sequence of treatment stages, each geometry being based on characteristics of the space that occur during subsequent ones of the treatment stages, by calculating deformation parameters based on the original pontic geometry, size characteristics of the space, and size characteristics of the first and second teeth at each of the treatment stages, to provide digital representations of stage-dependent pontic objects.

13. The computerized method of claim 12, wherein the original pontic geometry is selected from a library of geometries.

14. The computerized method of claim 13, wherein the library of geometries comprises at least one of current patient tooth geometries, prior patient tooth geometries, typodont tooth geometries, and pontic geometries.

15. The computerized method of claim 12, further comprising calculating a size of the space in each of the sequence of treatment stages.

16. The computerized method of claim 12, further comprising positioning a digital representation of the initial pontic object within the space.

17. The computerized method of claim 12, further comprising calculating the deformation parameters using uniform scaling.

18. The computerized method of claim 12, further comprising calculating the deformation parameters using non-uniform scaling.

19. The computerized method of claim 12, further comprising generating a deformed pontic geometry based on the deformation parameters.

20. The computerized method of claim 19, further comprising re-scaling the deformed pontic geometry.

21. The computerized method of claim 20, further comprising scaling the deformed pontic geometry based on scaling of at least one parameter comprising an X-scale parameter, a Y-scale parameter, and a Z-scale parameter, the at least one parameter being used with or without a Y-scale range parameter.

22. The computerized method of claim 12, wherein the step of determining whether the space is available for a pontic by measuring the distance from the closest point on each of the first and second teeth to the reference plane includes iterating each vertex on the first tooth to find a maximum signed distance (lMax) from each vertex on the first tooth to the reference plane, iterating each vertex on the second tooth to find a minimum signed distance (rMin) from each vertex on the second tooth to the reference plane, and calculating the space measurements at the stage i as the difference between rMin and lMax.

23. A computerized system for modeling a pontic to facilitate orthodontic treatment of teeth of a patient through a sequence of treatment stages, the computerized system comprising a processor configured for:
generating digital tooth models;
generating digital pontic models associated with the digital tooth models; and
facilitating the forming of pontics within a polymeric shell aligner, wherein generating digital pontic models comprises:

calculating space measurements of a digital representation of a space located between a first one of the digital tooth models having a first geometry and a second one of the digital tooth models having a second geometry by getting a first tooth transformation of the first digital tooth model at a given treatment stage i and a second tooth transformation of the second digital tooth model at the treatment stage i, wherein the first tooth defines a first coordinate system having a first Y-axis and the second tooth defines a second coordinate system having a second Y-axis;

applying the first tooth transformation to the first geometry and applying the second tooth transformation to the second geometry to get first and second positions of the first and second digital tooth models, respectively, at the stage i;

calculating a direction vector of the space measurements at the stage i, wherein the direction vector is derived from an interpolated Y-axis between the first Y-axis and the second Y-axis;

calculating a reference plane for the space measurements by using the direction vector as a normal;

determining whether the space is available for a pontic by measuring the distance from the closest point on each of the first and second teeth to the reference plane;

generating an original pontic geometry to provide a digital representation of an initial pontic object for use in a first stage of the sequence of treatment stages; and generating stage-dependent pontic geometries at each treatment stage during successive treatment stages of the sequence of treatment stages.

24. The computerized system of claim 23, wherein each geometry is based on characteristics of the space that occur during subsequent ones of the treatment stages, and the processor is further configured to calculate deformation parameters based on the original pontic geometry, size characteristics of the space, and size characteristics of the first and second teeth at each of the treatment stages, to provide digital representations of stage-dependent pontic objects.

25. The computerized system according to claim 23, wherein the processor is further configured to generate the stage-dependent pontic geometries by:
creating a stage change event;
sending a stage change event signal to an event monitor;
invoking an event handler of a pontic;
determining if a pontic is advisable at a selected one of the treatment stages;
obtaining pontic parameters from a parameter list; and
recalculating pontic geometry as appropriate.

* * * * *